United States Patent [19]

Wells

[11] Patent Number: 5,185,269
[45] Date of Patent: Feb. 9, 1993

[54] IMMUNOBEAD ASPIRATOR AND METHOD OF USE

[75] Inventor: John R. Wells, Culver City, Calif.

[73] Assignee: Source Scientific Systems, Inc., Garden Grove, Calif.

[21] Appl. No.: 479,766

[22] Filed: Feb. 13, 1990

[51] Int. Cl.⁵ .............................................. G01N 1/14
[52] U.S. Cl. .................................... 436/180; 422/99; 422/100; 435/287
[58] Field of Search ............... 435/291, 288, 7.1, 287; 436/180; 422/100, 63, 99; 134/21, 22.1, 25.4, 102, 182; 15/302; 73/863.21, 864, 864.01, 864.11

[56] References Cited

U.S. PATENT DOCUMENTS

| | | | |
|---|---|---|---|
| 4,053,284 | 10/1977 | Posch | 23/259 |
| 4,200,613 | 4/1980 | Alfrey et al. | 422/71 |
| 4,383,041 | 5/1983 | Kutsusawa et al. | 435/291 |
| 4,681,742 | 7/1987 | Johnson et al. | 422/102 |
| 4,754,771 | 7/1988 | Tangherlini et al. | 134/102 |
| 4,803,050 | 2/1989 | Mack | 422/65 |
| 4,816,408 | 3/1989 | Suzuki et al. | 435/311 |
| 4,913,179 | 4/1990 | Engel et al. | 134/113 |

Primary Examiner—Robert J. Warden
Assistant Examiner—William H. Beisner
Attorney, Agent, or Firm—Donald G. Lewis

[57] ABSTRACT

The immunobead aspirator reduces the amount of carry over liquid which remains within a test tube or other immunoassay vessel after an aspiration procedure. When the immunobead aspirator lifts up the immunobead during the aspiration procedure, the immunobead contacts an array of protuberances within an inverted bowl from which a vacuum is drawn. The array of protuberances define a hollow which exceeds the size of the immunobead. Accordingly, at any given time, the immunobead makes limited contact with only a portion of the protuberances. This reduces the amount of liquid which is trapped within points of contact between the lifted immunobead and the aspiration device and reduces the amount of carry over liquid.

5 Claims, 1 Drawing Sheet

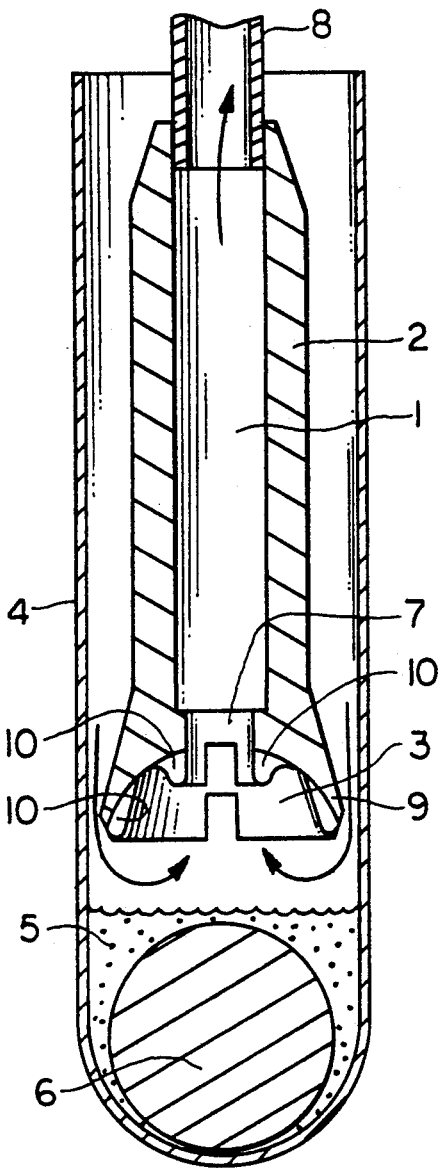
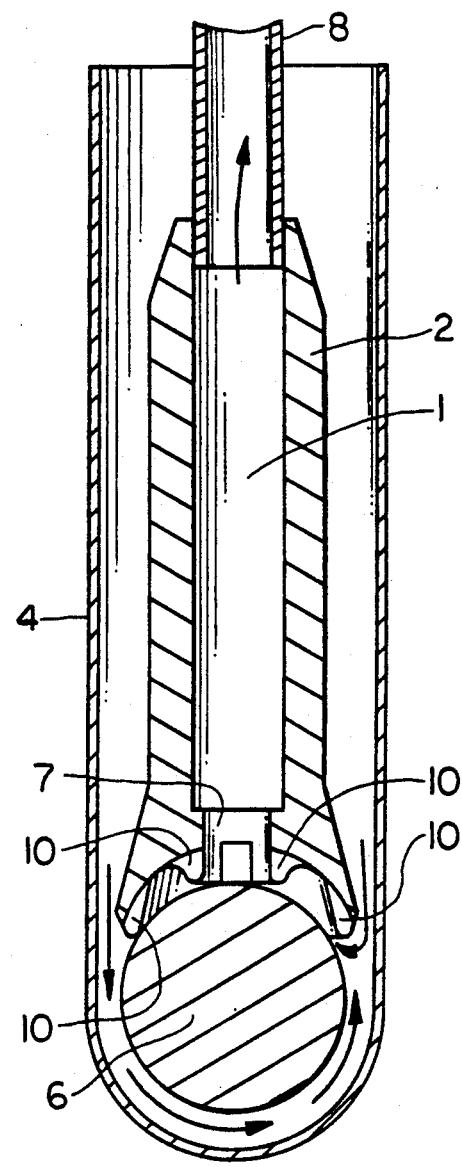
FIG. 1    FIG. 2
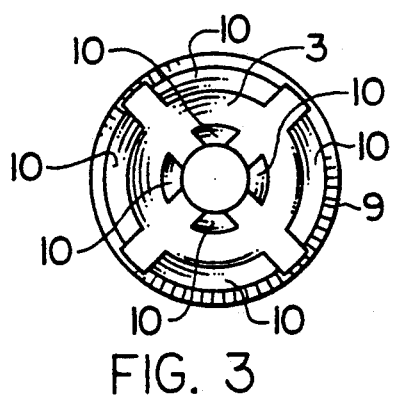
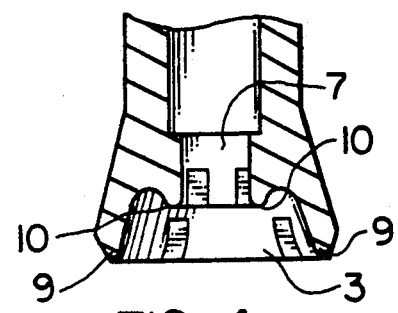
FIG. 3    FIG. 4

IMMUNOBEAD ASPIRATOR AND METHOD OF USE

BACKGROUND OF THE INVENTION

The invention relates to aspiration devices for use with immunoassays of the type which employ immunobeads or immunoballs. More particularly, the invention relates to devices for aspirating fluids from test tubes, microtiter wells, or other immunoassay incubation vessels which contain immunobeads or immunoballs and which enhance the completion of the aspiration process by picking up the immunobead or immunoball.

For a conventional immunoassay, multiple liquids must be dispensed and aspirated from an immunoassay reaction vessel. The automation of immunoassays requires the mechanization of such multiple liquid dispensing and aspiration steps. The reliability of the immunoassay is dependent upon the accuracy of the dispensing steps and the completeness of the aspiration steps. Incomplete aspiration may result in the carry over of unreacted or unbound species from one step in the assay to the next. Such carry over may necessitate further wash steps or may result in the introduction of inaccuracy.

Immunoassays which employ immunobeads or immunoballs can be particularly difficult to aspirate completely. It has been found that lifting the immunobead or immunoball during the aspiration procedure reduces the amount of carry over liquid which remains between the immunobead and the bottom of the immunoassay incubation vessel. Aspirators having an inverted bowl may be employed for lifting the immunobead during such aspiration procedures. If a vacuum is pulled from this inverted bowl, the inverted bowl can lift the immunobead. To facilitate the capture of the immunobead, the inverted bowl may be given a shape which is complementary to the shape of the immunobead, i.e. the immunobead may fit snugly into the inverted bowl. To prevent the clogging of the vacuum port by the immunobead, longitudinal channels may be formed within the inverted bowl extending from the vacuum port to the rim. Aspirated liquids may travel within these channels to the vacuum source. The aspiration of liquids is also facilitated if the rim of the inverted bowl extends proximally to the side walls of the immunoassay incubation vessel. Accordingly, it has been found that liquids may be aspirated from the bottom of the vessel by lifting and capturing the immunobead and by then drawing the vacuum proximally to the wall of the vessel through these channels.

Unfortunately, the capture of the immunobead by the inverted bowl can cause liquid to be trapped within the contact area between the immunobead and the inverted bowl. Such trapped liquid can cause incomplete aspiration and liquid carry over.

What is needed is an aspiration device for use with immunobeads and immunoballs which can reduce the amount liquid carry over between aspiration steps.

SUMMARY

The immunobead aspirator reduces the volume of carry over liquid by reducing the contact area between the immunobead and the inverted bowl. The immunobead aspirator employs an array of protuberances within the inverted bowl. The array of protuberances contacts the immunobead when it is lifted by the aspirator. However, the contact between the protuberances and the immunobead is not snug. The array of protuberances define a hollow which is larger than the immunobead. Accordingly, the immunobead can not contact all of the protuberances simultaneously.

In a preferred embodiment, the immunobead has only point contact with the protubrances, as opposed to surface contact, i.e. the contact between the immunobead and the protuberances is limited to two or more points.

In a further preferred embodiment, the immunobead may be jostled during the aspiration process so that the points of contact between the immunobead and the protuberances may change several times during a single aspiration procedure. During a single aspiration procedure, such jostling can allow the entire surface of the immunobead to be free of contact with the protuberances at some point during the procedure. Accordingly, the carry over is further reduced.

BRIEF DESCRIPTION OF THE DRAWINGS.

FIG. 1 is a sectional view of a test tube containing a liquid, an immunobead, and a portion of an immunobead aspirator. The immunobead aspirator has not yet captured the immunobead in FIG. 1.

FIG. 2 is an other sectional view of the assembly of FIG. 1. However, the aspirator has been further lowered into the test tube, the immunobead has been captured and the aspiration of the liquid has been largely completed. Note that the immunobead contacts only the protuberances on the left hand side of the inverted bowl in FIG. 2.

FIG. 3 is a plan view of the inverted bowl and protuberances of FIGS. 1 and 2 viewed from the bottom and rotated 45 degrees.

FIG. 4 is a fragment of a sectional view of the inverted bowl and protuberances of FIG. 3.

DETAILED DESCRIPTION THE APPARATUS

The preferred embodiment of the aspirator (1) is shown in FIGS. 1-4. The aspirator (1) includes a neck (2) and an inverted bowl (3). The neck (2) is connected to the inverted bowl (3) and serves to extend the inverted bowl (3) into the test tube (4), microtiter well, or other immunoassay vessel for aspirating liquid (5) therefrom and for lifting the immunobead (6). The neck (2) is hollow. The hollow portion of the neck (2) is connected at one end to the inverted bowl (3) by means of a vacuum port (7) and to the opposite end to a vacuum source (8). The vacuum port (7) enables air and liquid (5) to be drawn from the test tube (4) through said inverted bowl (3) and said neck (2) and into the vacuum source (8).

The inverted bowl (3) faces downward as the aspirator (1) is inserted into the test tube (4). The inverted bowl (3) has a concave shape. The rim (9) of the inverted bowl (3) extends nearly to the wall of the test tube (4) or other vessel. The vacuum port (7) opens onto or near the apex of the inverted bowl (3). Accordingly, when the vacuum source (8) is activated, air is drawn around the rim (9) of the inverted bowl (3) and into the vacuum port (7). As the inverted bowl (3) is lowered toward the immunobead (6), the immunobead (6) is lifted from the bottom of the test tube (4) by the vacuum and drawn into the inverted bowl (3). The immunobead (6) will remain captured within the inverted bowl (3) for as long as the vacuum source (8) is activated.

The invention teaches that the volume of carry over liquids may be reduced by the addition of an array of protuberances (10) within the inverted bowl (3). This array of protuberances (10) contacts the immunobead (6) when it is drawn into the inverted bowl (3) and provides a gap between the immunobead (6) and the inverted bowl (3) so that air and liquid may continue to be drawn through the inverted bowl (3) even when it contains the immunobead (6).

In the preferred embodiment, the array of protuberances (10) defines a hollow which is materially greater in size than the immunobead (6). Accordingly, the fit between the immunobead (6) and the protuberances (10) is loose, i.e. it is not snug. The captured immunobead (6) can not simultaneously contact all of the protuberances (10) within the inverted bowl (3), i.e. the immunobead (6) must lack contact with at least one protuberance (10) within the inverted bowl (3) at any given time.

In a preferred embodiment, the array of protuberances (10) including a first segmented annulus proximal to said vacuum port (7) and a second segmented annulus distal from said vacuum port (7), i.e. proximal to the rim (9). Each of these annuluses have a radius of curvature which materially exceeds that of the immunobead (6). It is possible to adapt this configuration of protuberances (10) so as to allow the immunobead (6) to be jostled from one contact position to an other during a single aspiration procedure. When such jostling occurs, all points of contact may be freed at one time or another during a single aspiration procedure. Accordingly, the volume of trapped liquid (5) may be further reduced.

In an other preferred embodiment, the array of protuberances (10) adapted so that the contact between the immunobead (6) and the protuberances (10) may include point contacts as opposed to surface contacts. For example, FIG. 2 illustrates the immunobead (6) having tangential contact with the annular protuberances (10).

The Method

The use of an array of protuberances (10) as described above facilitates the aspiration of liquid from the vessel by reducing the amount of carry over liquid (5) which may be trapped between the immunobead (6) and the inverted bowl (3) during an aspiration procedure.

In a preferred aspiration procedure, the aspiration device is lowered into the test tube (4) or other immunoassay incubation vessel with the inverted bowl (3) facing downward, i.e. toward the liquid (5). The aspiration device is lowered until the rim (9) of the inverted bowl (3) is immersed in liquid (5). Meanwhile, the vacuum source (8) is activated. When the vacuum source (8) actived, liquid (5) is aspirated from the test tube (4). To continue the aspiration process, the aspiration device is lowered until it approaches the immunobead (6). Prior to reaching the immunobead (6), the immunobead (6) is lifted by the vacuum of the aspiration device and is captured within the inverted bowl (3). Once captured by the inverted bowl (3), the immunobead (6) makes contact with the protuberances (10) within the inverted bowl (3). The protuberances (10) prevent the clogging of the vacuum port (7) by means of the immunobead (6) and provide a a gap between the immunobead (6) and the inverted bowl (3). Accordingly, liquid (5) may continue to be aspirated into the inverted bowl (3).

Since the protuberances (10) define a hollow greater in size than the immunobead (6), the immunobead (6) will not contact all of the protuberances (10) simultaneously. Accordingly, there is less contact area between the immunobead (6) and the protuberances (10) as compared to the situation in which there was a tight fit between the immunobead (6) and the protuberances (10).

Once the immunobead (6) is lifted, the aspiration is continued with liquid (5) being drawn from the bottom of the test tube (4) and from the immunobead (6) itself. In particular, the aspirated liquid may include liquid which lies between the immunobead (6) and one or more protuberances (10) with which the immunobead (6) is not in contact.

After the aspiration is complete, the vacuum source (8) may be deactivated. Deactivation of the vacuum source (8) allows the immunobead (6) to drop from the aspiration device back into the vessel. The aspiration device may then be raised and removed from the test tube (4).

What is claimed is:

1. In a device for aspirating liquid from a vessel containing an immunobead by means of a vacuum source, the device including:

an inverted bowl defining a vacuum port and
a hollow neck connected to the vacuum port of
said inverted bowl and connectable to the vacuum source for providing passage for liquid and air through the vacuum port and into the vacuum source,
said neck for connecting to the vacuum source and extending said inverted bowl into the vessel for aspirating liquid therefrom and for capturing and lifting the immunobead therefrom into said inverted bowl during such liquid aspiration process, the improvement comprising:

an array of protuberances arising from within said inverted bowl exclusive of the vacuum port for contacting the immunobead and for providing a gap between the immunobead and said inverted bowl for aspirating liquid and drawing air from the vessel into the vacuum source while the immunobead is captured within said inverted bowl during the liquid aspiration process, said array of protuberances defining a hollow greater in size than the immunobead such that the immunobead cannot contact all of the protuberances simultaneously and must lack contact with at least one protuberance at any given time, whereby the use of said array of protuberances facilitates the aspiration of liquid from the vessel and reduces the amount of liquid which may be trapped between the immunobead and said inverted bowl during the liquid aspiration process.

2. In a device as described in claim 1 wherein,
said array of protuberances including a first segmented annulus proximal to said vacuum port and a second segmented annulus distal from said vacuum port,
said first and second segmented annuluses each having a radius of curvature greater than the immunobead.

3. In a device as described in claim 1 wherein,
said array of protuberances adapted to having point contact with the immunobead.

4. In a device as described in claim 1 wherein,
said array of protuberances adapted to having contact with the immunobead which may be jostled from one point on said array of protuberances to another.

5. In a method of aspirating liquid from a vessel containing an immunobead, the method including the steps:

Step 1: providing a vacuum source, an aspiration device having an inverted bowl, and a vessel containing an immunobead, Step 2: lowering the aspiration device into the vessel; while, Step 3: activating the vacuum source for drawing a vacuum through the aspiration device; then Step 4: aspirating liquid from the vessel above the immunobead by means of the aspiration device; then Step 5: lifting and capturing the immunobead by means of the vacuum into the inverted bowl within the aspiration device; then Step 6: aspirating liquid from the vessel below the immunobead; then Step 7: deactivating the vacuum source and allowing the immunobead to drop from the aspiration device back into the vessel; and then Step 8: raising the aspiration device out of the vessel;

wherein the improvement comprises:

in said Step 5, the captured immunobead making contact with an array of protuberances arising from the inverted bowl exclusive of the vacuum port, each of the protuberances being contactable with the captured immunobead but collectively forming a hollow greater in size than the immunobead such that the immunobead cannot contact all of the protuberances simultaneously and must lack contact with at least one protuberance at any given time, in said Step 6: aspirating liquid from the vessel including liquid which lies between the immunobead and one or more protuberances with which the immunobead is not in contact.

* * * * *